US012751633B2

(12) United States Patent
Mori et al.

(10) Patent No.: US 12,751,633 B2
(45) Date of Patent: Oct. 6, 2026

(54) BIOMETRIC INFORMATION MEASURING DEVICE

(71) Applicant: OMRON HEALTHCARE Co., Ltd., Kyoto (JP)

(72) Inventors: Kentaro Mori, Kyoto (JP); Takeshi Kubo, Kyoto (JP); Yasuo Asano, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 236 days.

(21) Appl. No.: 18/487,760

(22) Filed: Oct. 16, 2023

(65) Prior Publication Data

US 2024/0032804 A1 Feb. 1, 2024

Related U.S. Application Data

(63) Continuation of application No. PCT/JP2021/020448, filed on May 28, 2021.

(51) Int. Cl.

*A61B 5/0205* (2006.01)
*A61B 5/00* (2006.01)
(Continued)

(52) U.S. Cl.

CPC ........ *A61B 5/0205* (2013.01); *A61B 5/02116* (2013.01); *A61B 5/02141* (2013.01);
(Continued)

(58) Field of Classification Search

None
See application file for complete search history.

(56) References Cited

U.S. PATENT DOCUMENTS

2006/0264771 A1* 11/2006 Lin ..................... A61B 5/0205 600/513
2012/0283583 A1* 11/2012 Batkin .................. A61B 5/025 600/499
2016/0029908 A1 2/2016 Usuda et al.

FOREIGN PATENT DOCUMENTS

JP 2007-195693 A 8/2007
JP 2014-36843 A 2/2014
(Continued)

OTHER PUBLICATIONS

International Search Report (ISR) for International Application No. PCT/JP2021/020448, Dated Aug. 17, 2021.
(Continued)

*Primary Examiner* — Ankit D Tejani
(74) *Attorney, Agent, or Firm* — Colson Law Group, PLLC

(57) ABSTRACT

A biometric information measuring device includes a blood pressure measurement unit including a cuff configured to compress a target measurement site of a subject, a pump configured to supply a gas into the cuff, an exhaust valve configured to adjust discharge of the gas from within the cuff, a pressure detection unit configured to detect a cuff pressure that is a pressure in the cuff, a cuff pressure control unit configured to control the pump and the exhaust valve, and a blood pressure calculation unit configured to calculate a blood pressure of the subject, the blood pressure measurement unit being configured to measure the blood pressure of the subject, an electrocardiographic measurement unit being configured to process an electrical signal acquired through a plurality of electrodes contactable to a skin of the subject to measure an electrocardiographic waveform.

5 Claims, 13 Drawing Sheets

(51) Int. Cl.
*A61B 5/021* (2006.01)
*A61B 5/318* (2021.01)
*G16H 40/63* (2018.01)

(52) U.S. Cl.
CPC ............ *A61B 5/318* (2021.01); *A61B 5/7235* (2013.01); *A61B 5/7271* (2013.01); *G16H 40/63* (2018.01); *A61B 2560/02* (2013.01)

(56) References Cited

FOREIGN PATENT DOCUMENTS

| | | | | | |
|---|---|---|---|---|---|
| JP | 2020-28421 | A | | 2/2020 | |
| WO | WO-2020039830 | A1 | * | 2/2020 | ............. A61B 5/742 |

OTHER PUBLICATIONS

International Preliminary Report (IPRP) for International Application No. PCT/JP2021/020448, Dated Feb. 10, 2022.

Office Action issued on Nov. 4, 2025 in corresponding IN patent application No. 202317066932.

* cited by examiner

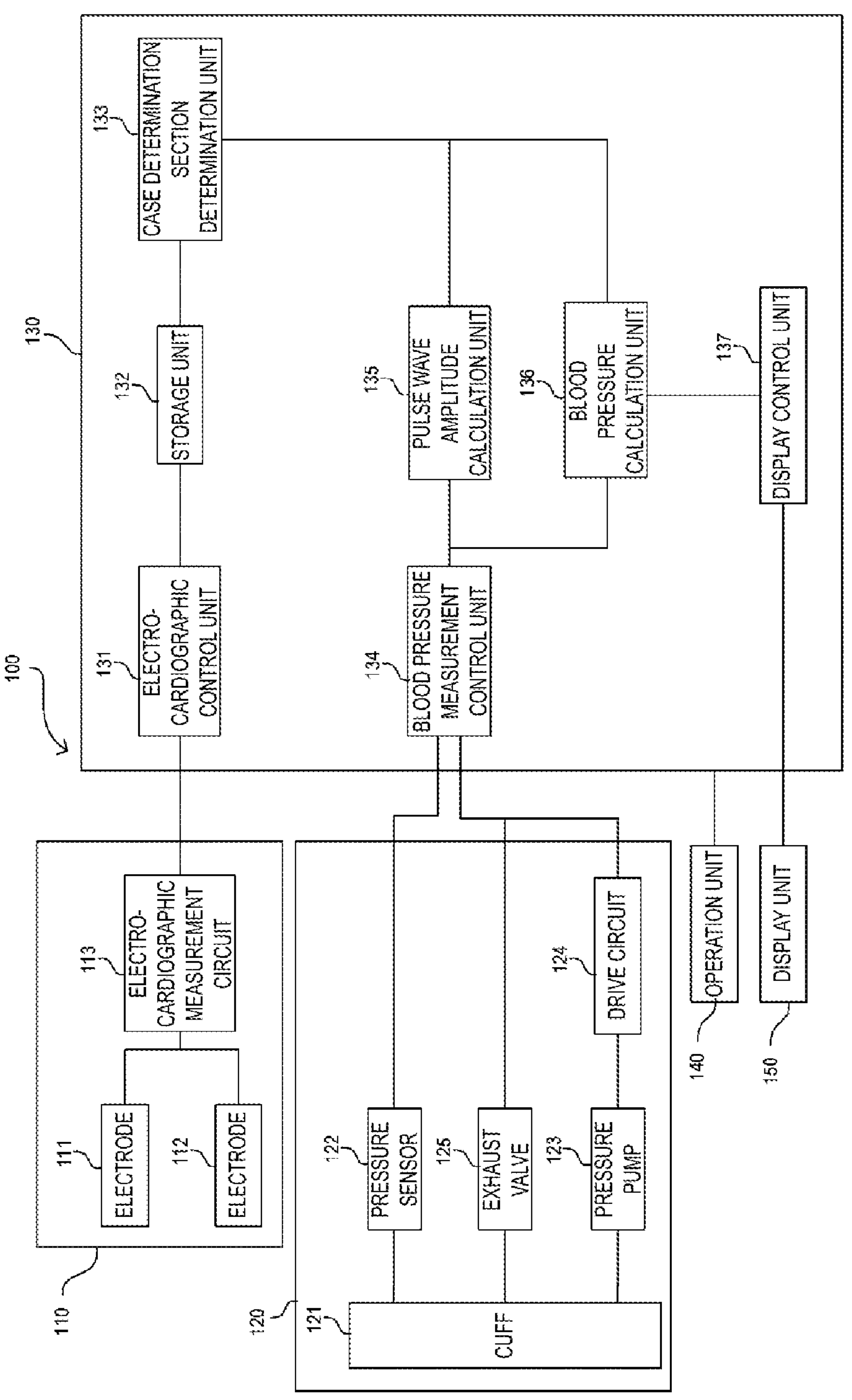
[FIG. 1]

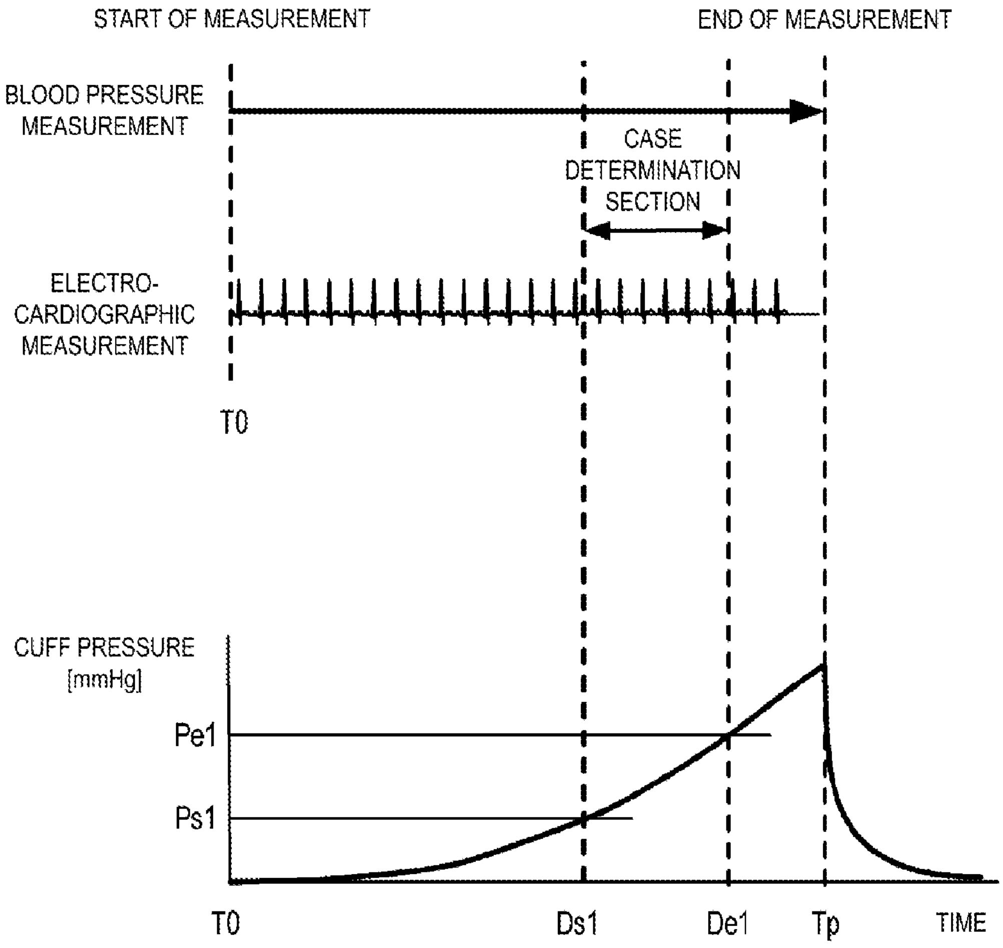
[FIG. 2]

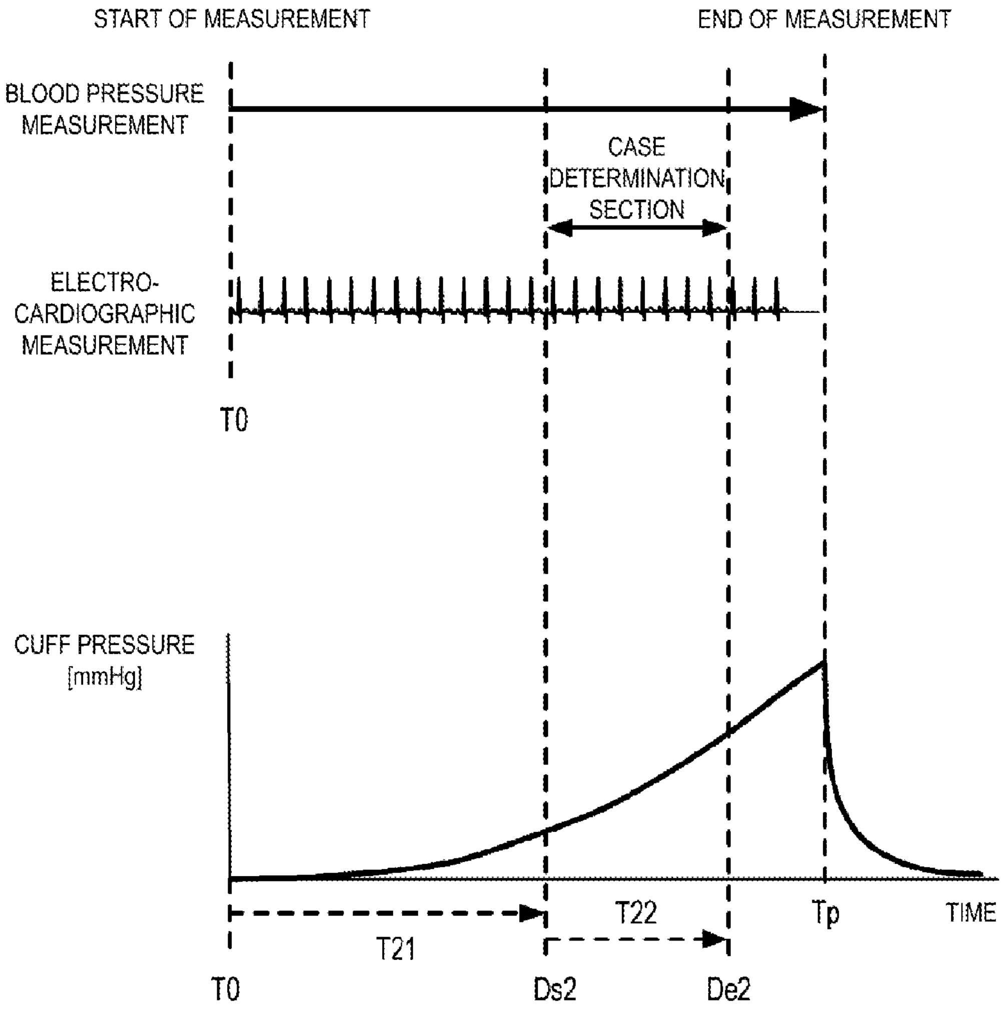
[FIG. 3]

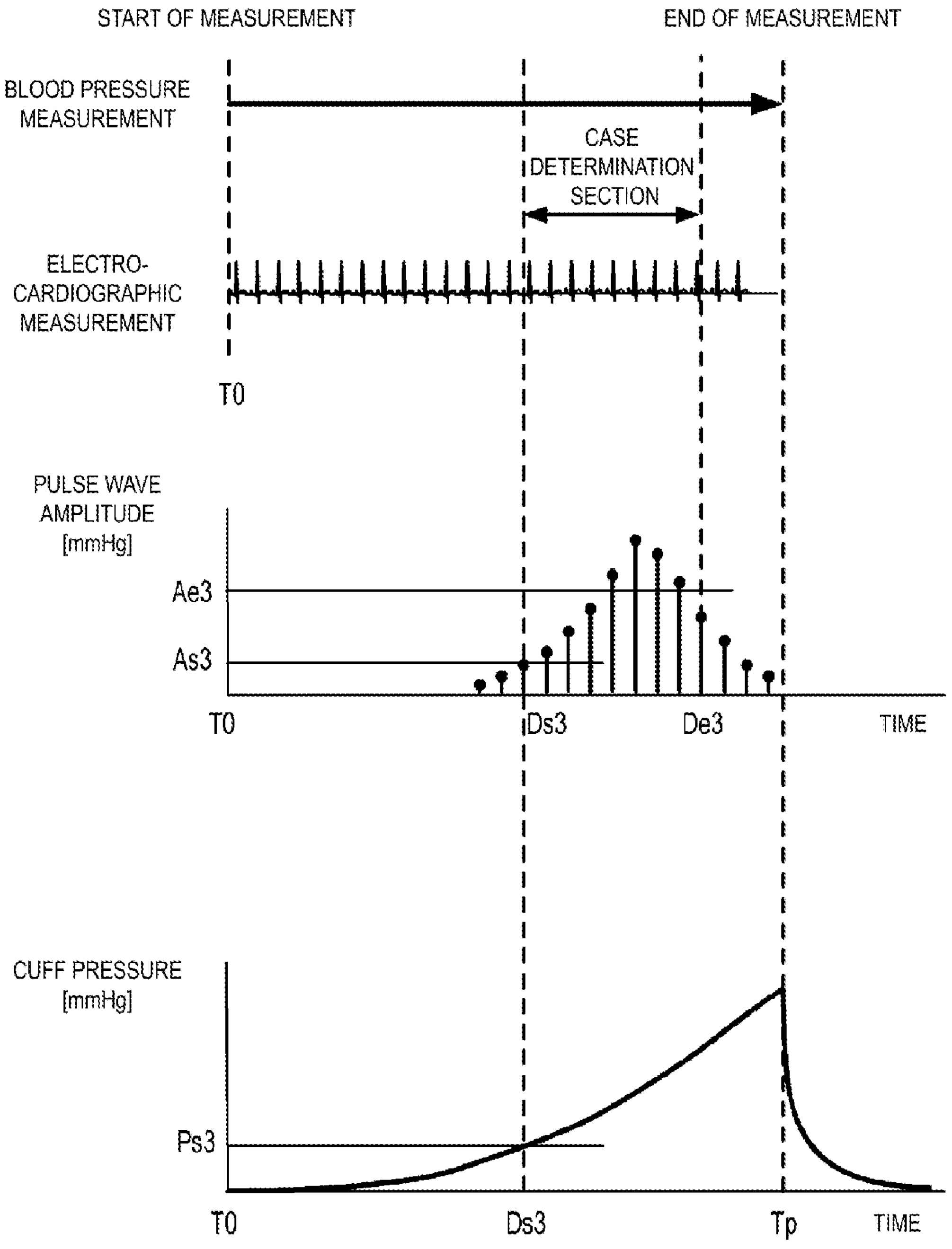
[FIG. 4]

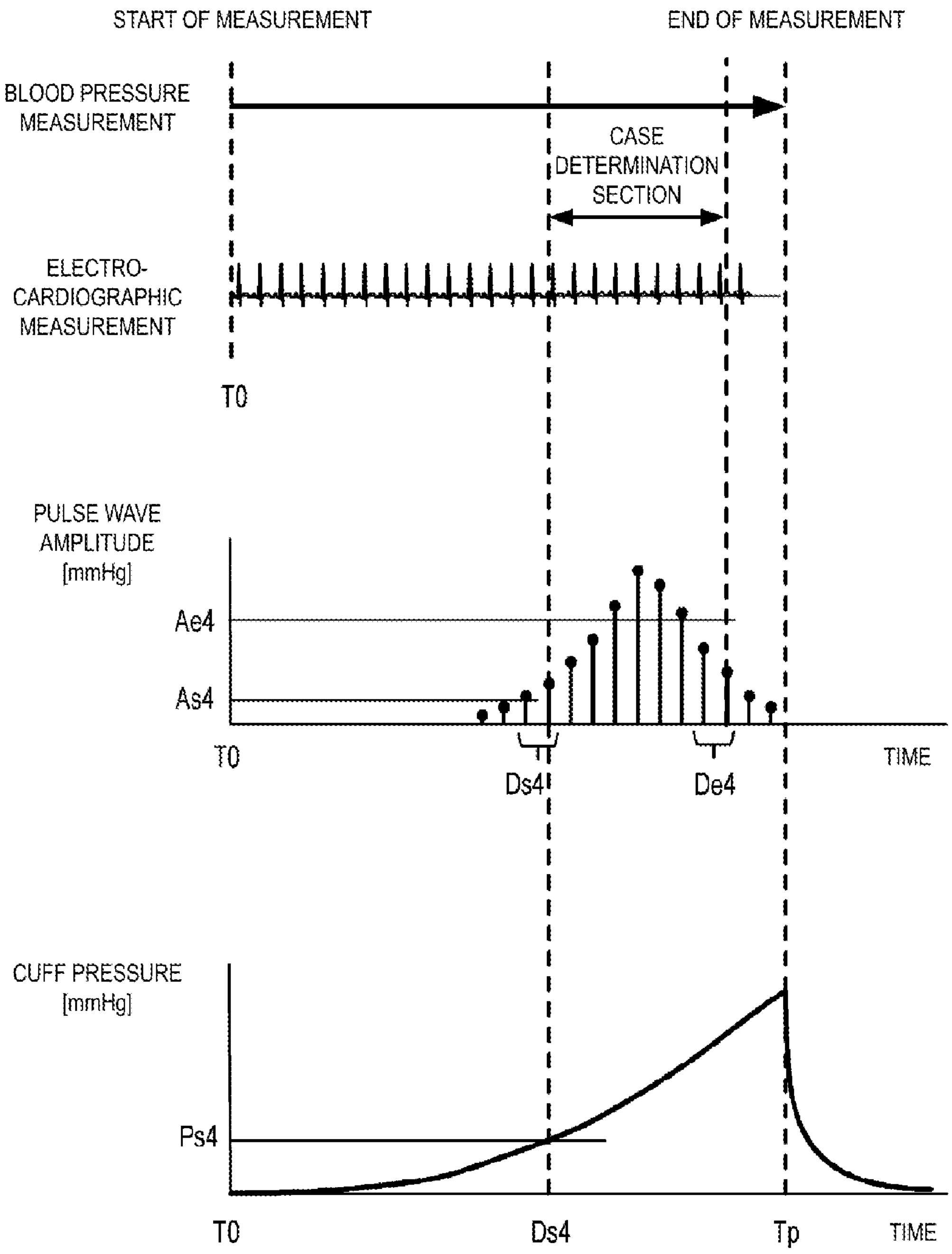
[FIG. 5]

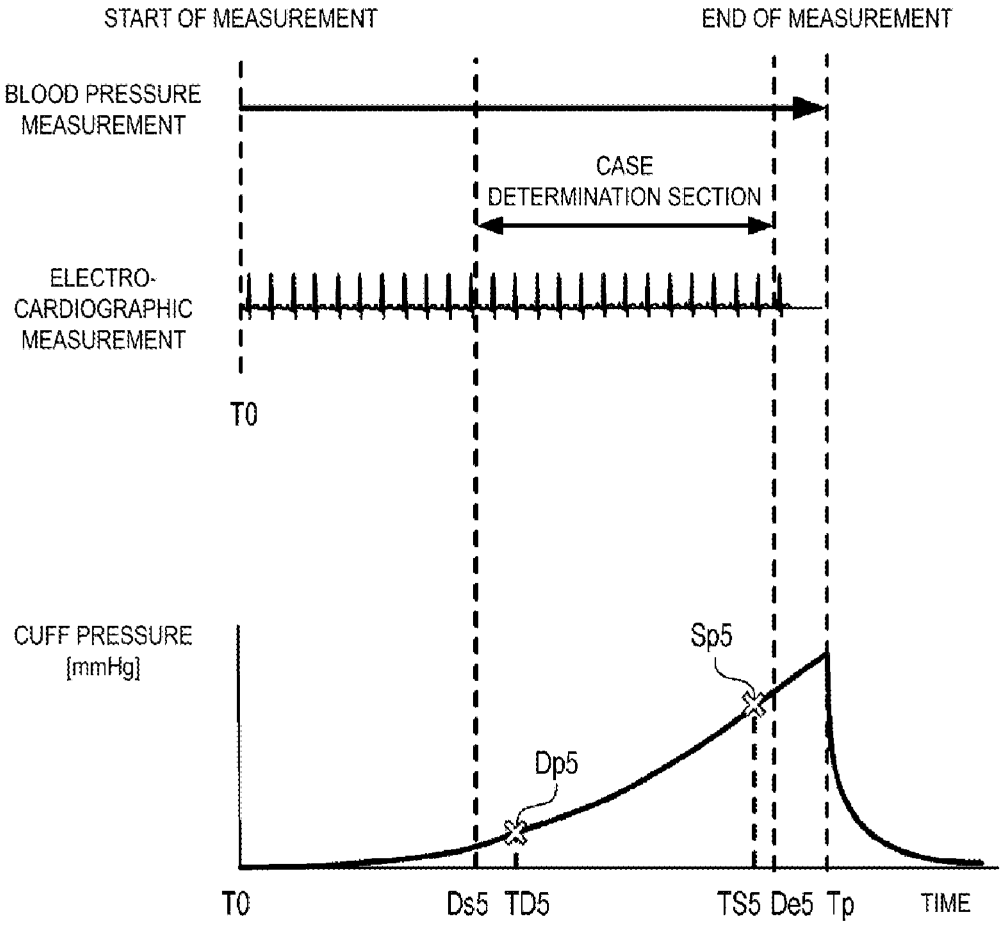
[FIG. 6]

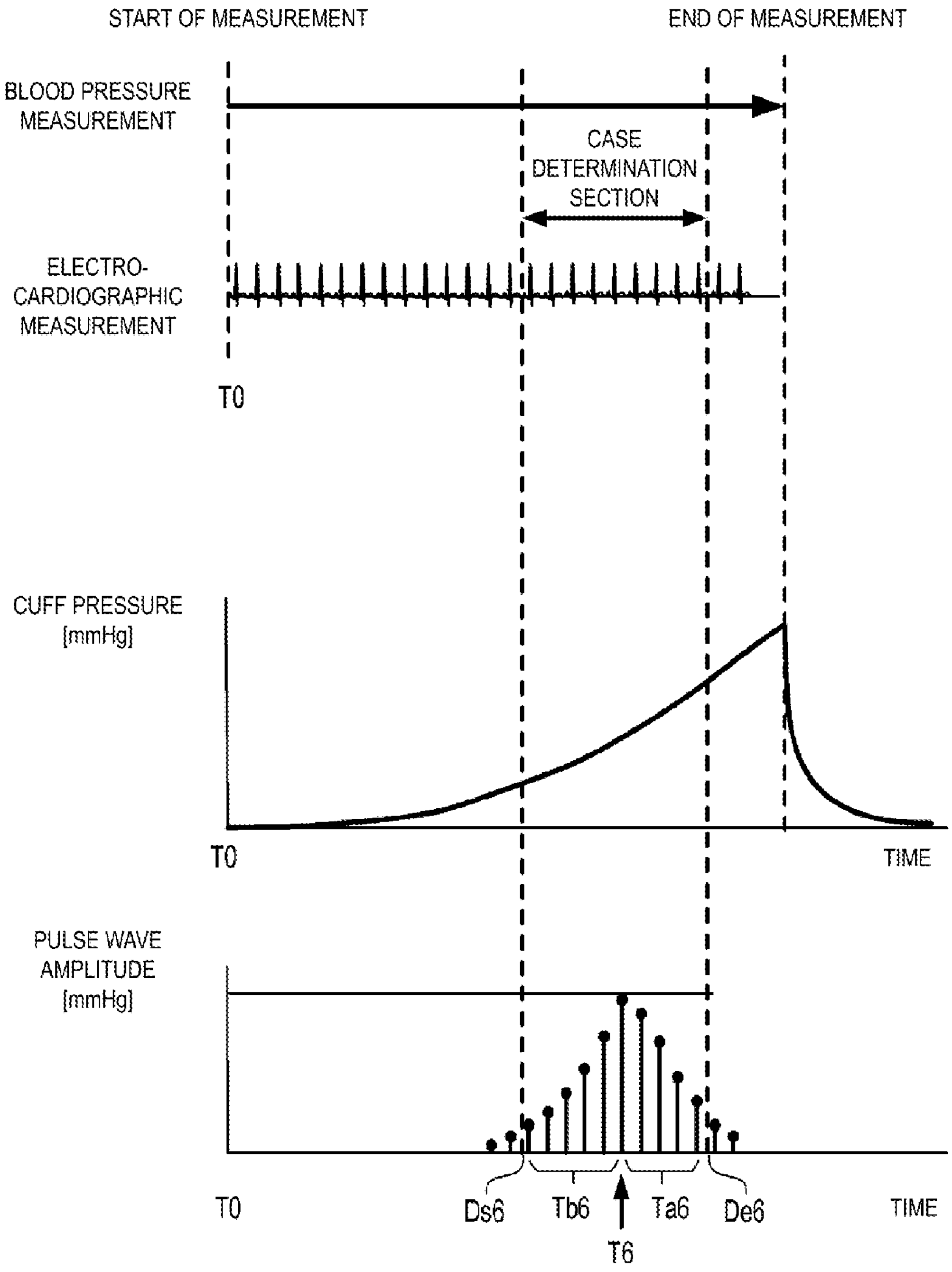
[FIG. 7]

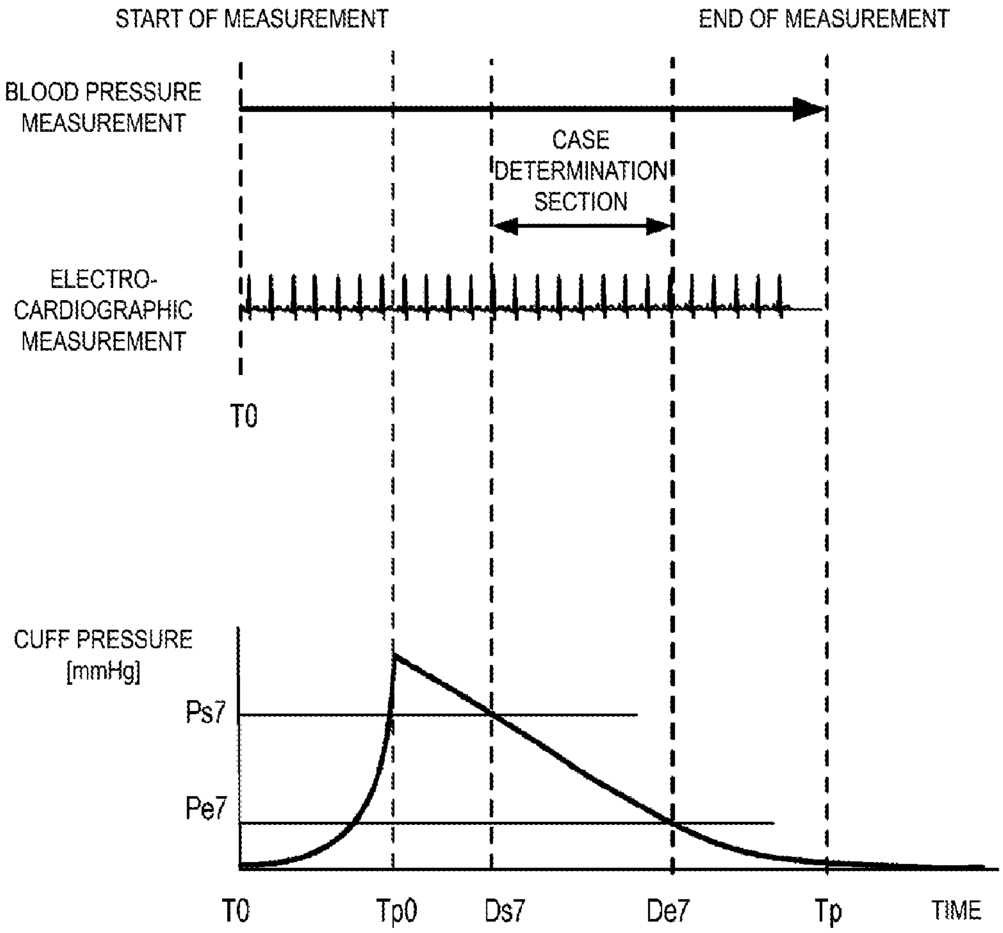
[FIG. 8]

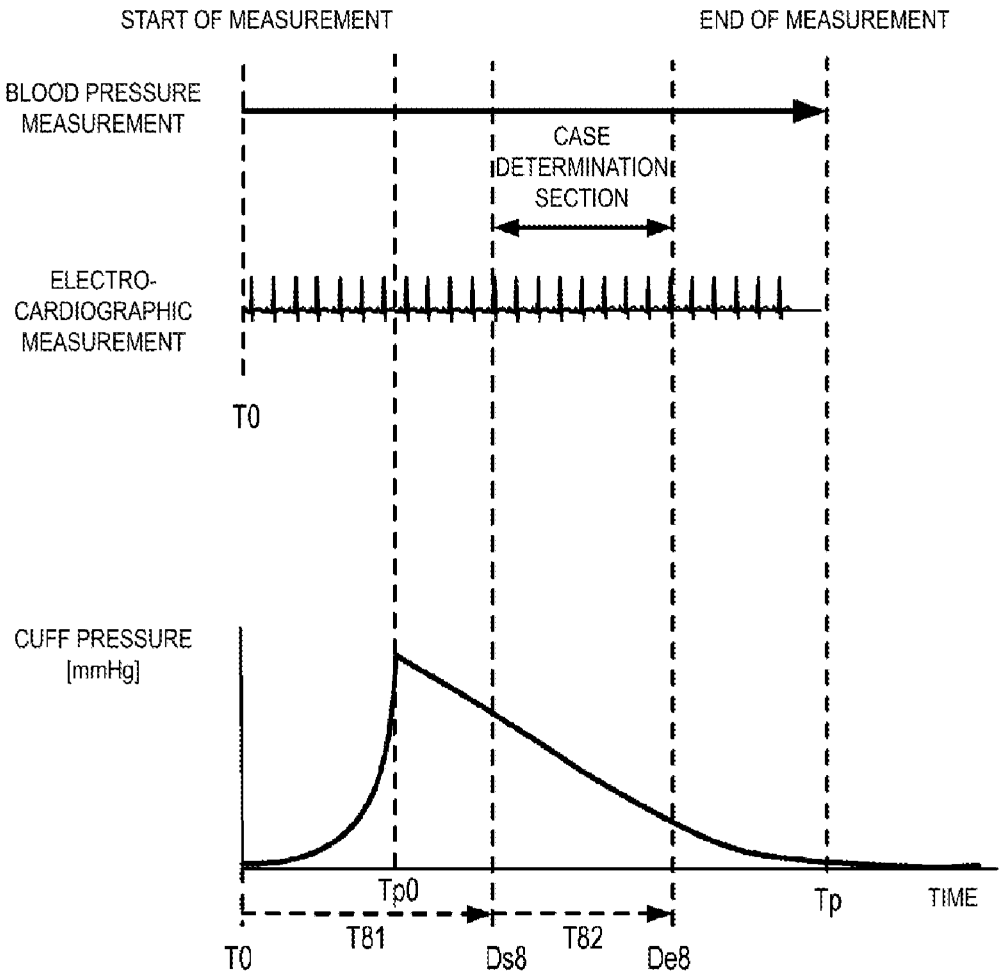
[FIG. 9]

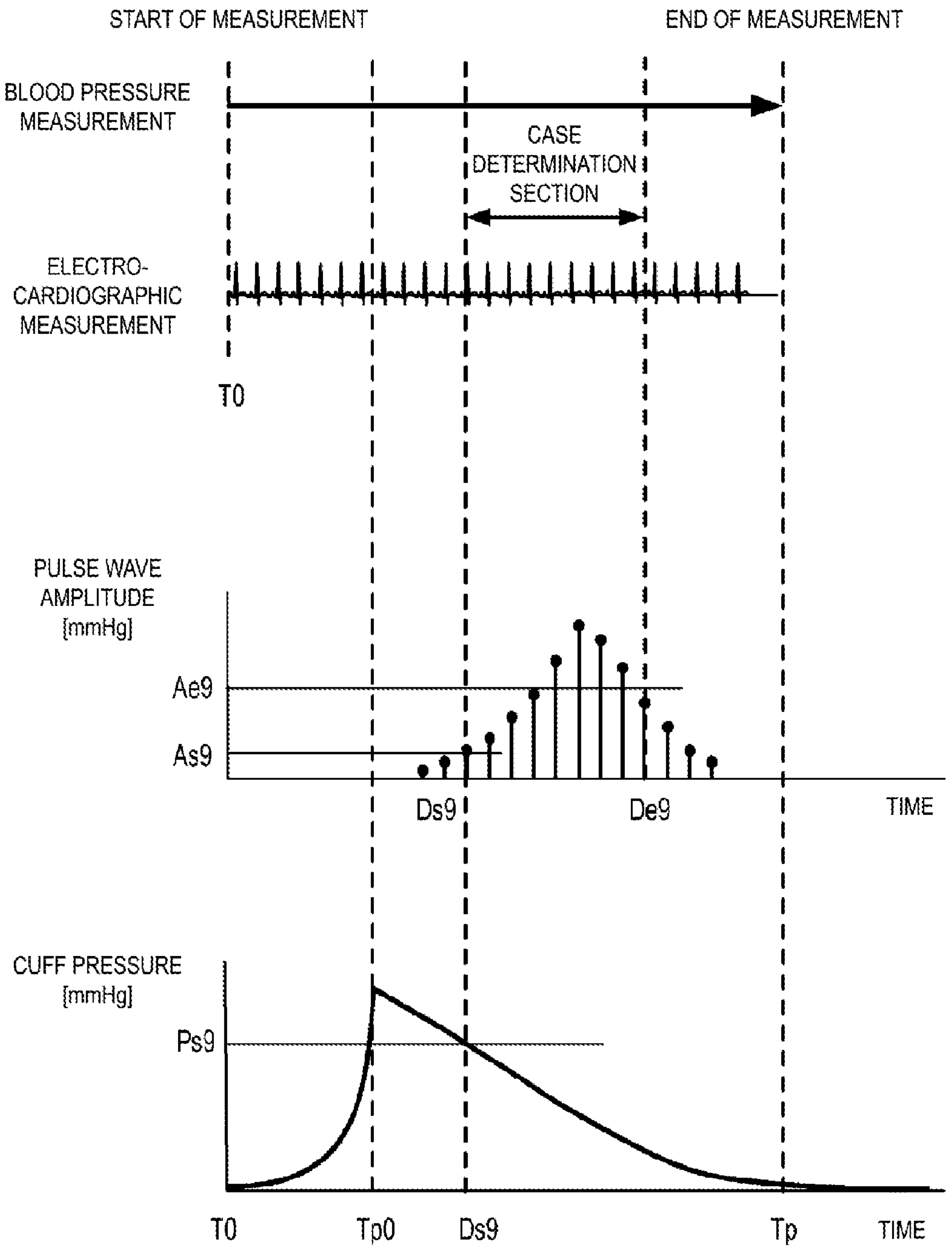
[FIG. 10]

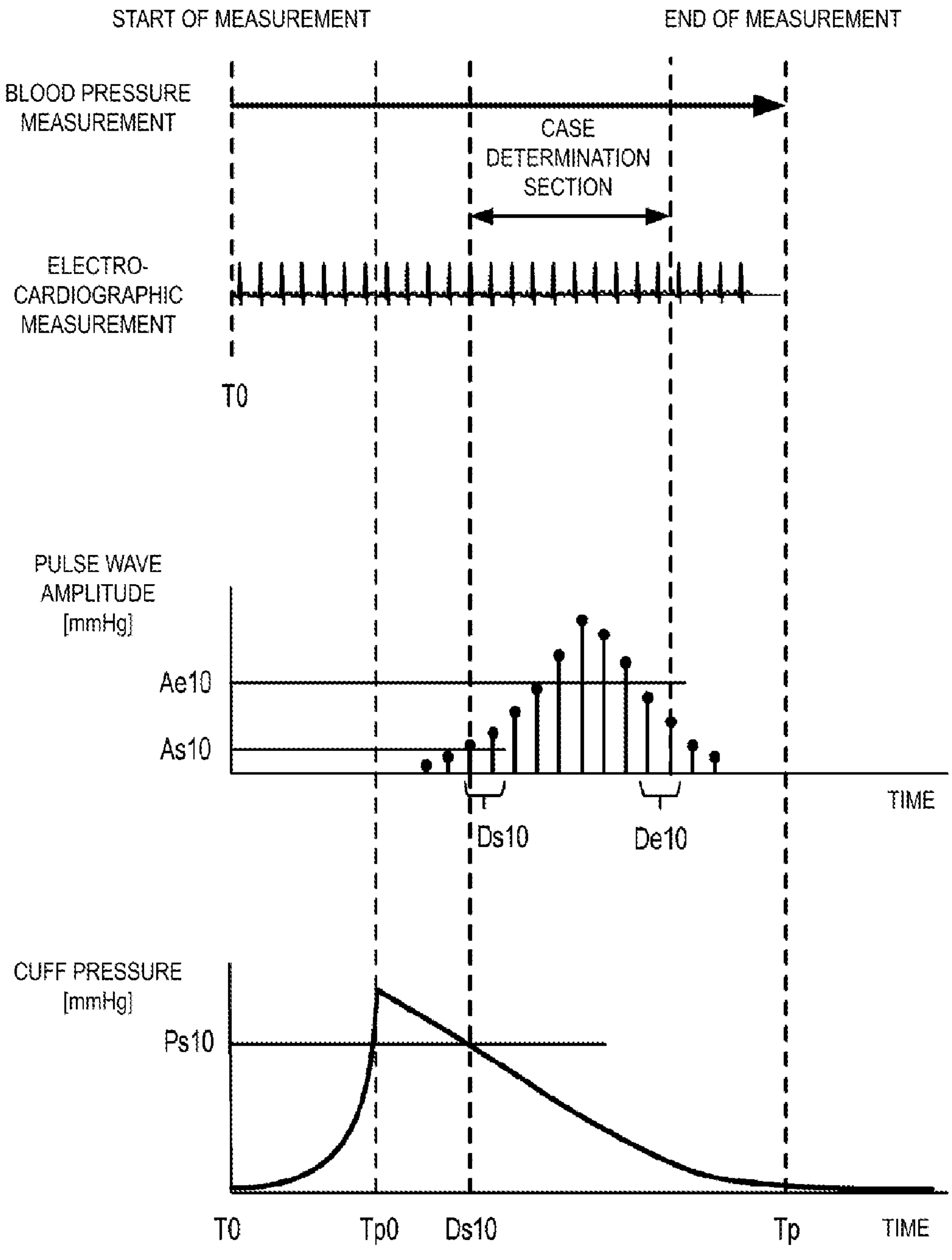
[FIG. 11]

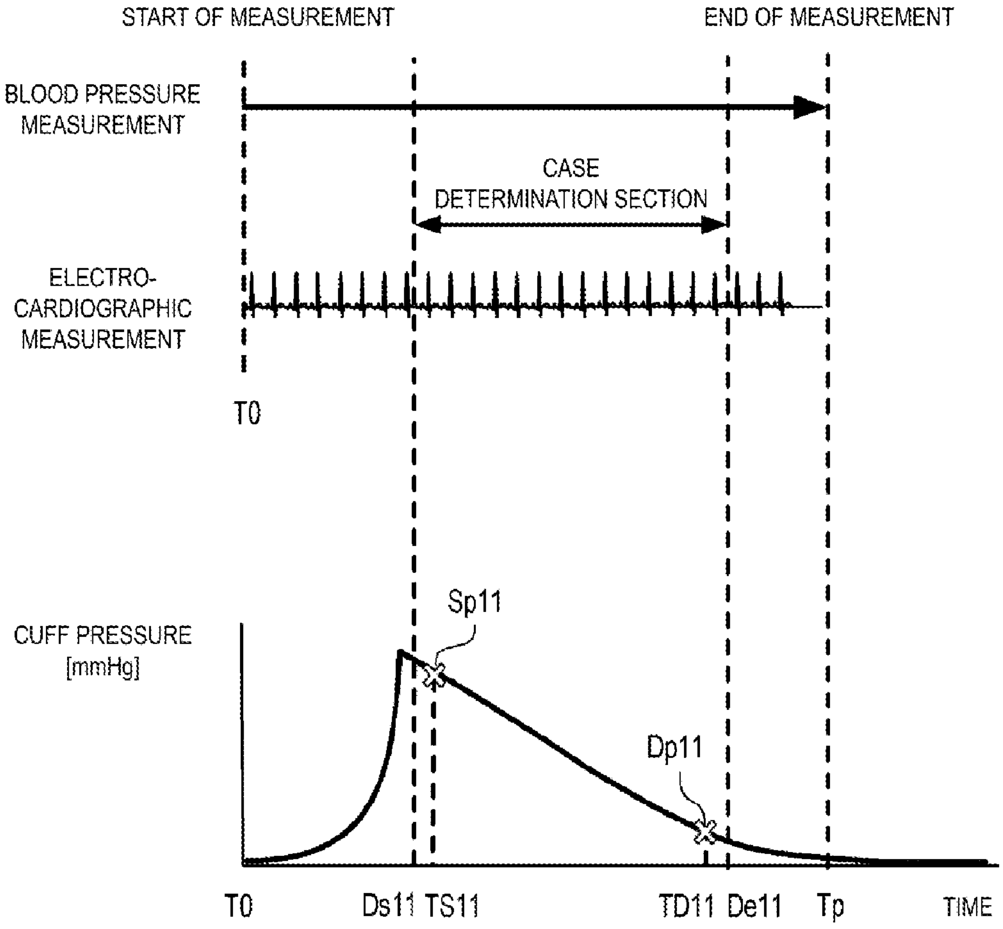
[FIG. 12]

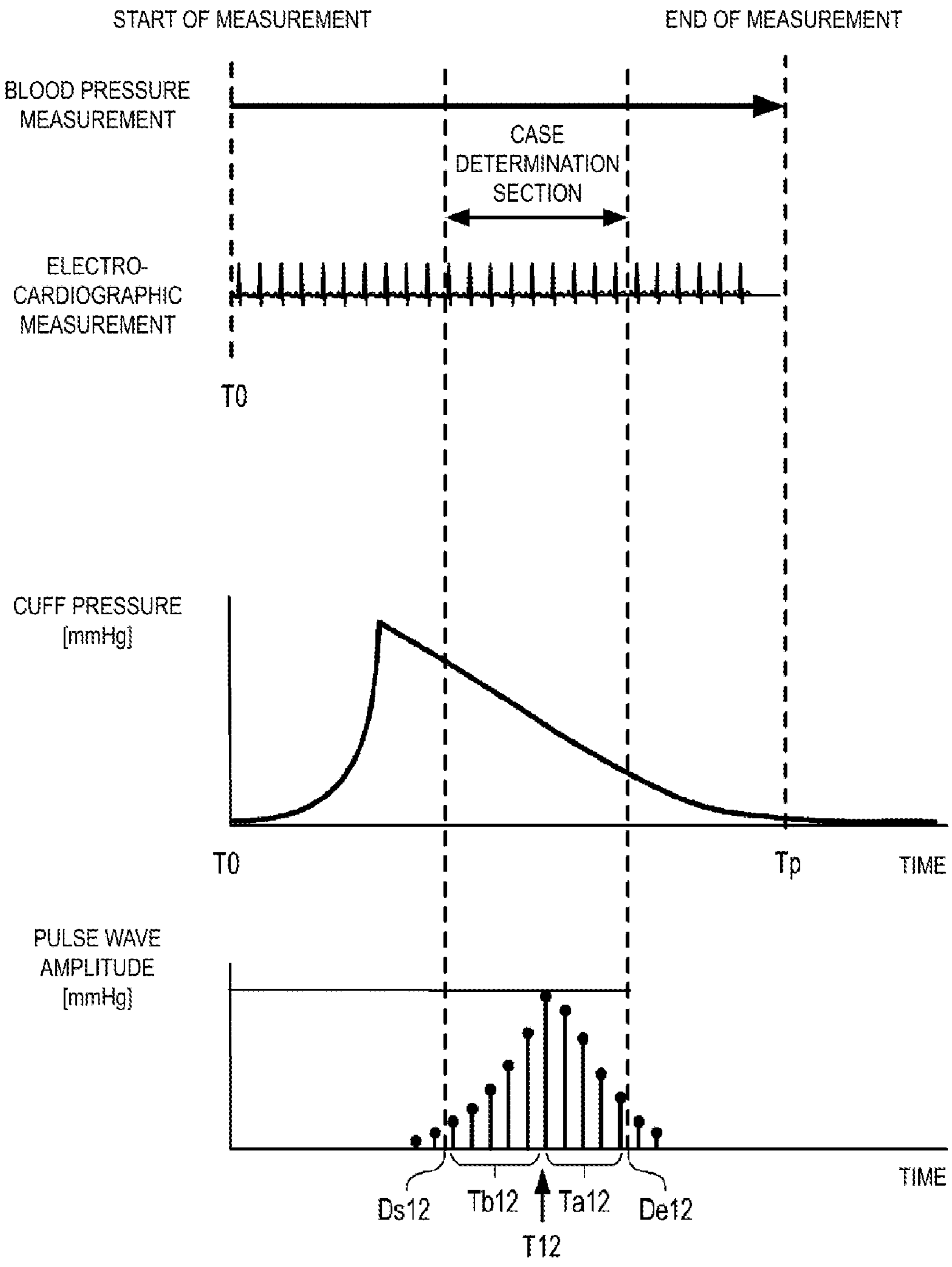
[FIG. 13]

BIOMETRIC INFORMATION MEASURING DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2021/020448, filed May 28, 2021, which application is incorporated herein by reference in its entirety.

TECHNICAL FIELD

The present invention relates to a biometric information measuring device.

BACKGROUND ART

This section references patent document, i.e., Citation: Patent Document 1: JP 2014-36843 A (hereinafter Patent Document 1). A device illustrated in Patent Document 1 has been proposed as a device by adding an electrocardiographic measurement function to a conventional cuff-pressure-type blood pressure monitor.

SUMMARY OF INVENTION

Technical Problem

However, in the conventional configuration in which electrocardiographic measurement is performed when a pressure in a cuff is stable, it is necessary to change the pressure in the cuff at the time of blood pressure measurement, and thus electrocardiographic measurement cannot be performed simultaneously with blood pressure measurement. In particular, when electrocardiographic measurement is performed simultaneously with blood pressure measurement, in the state of insufficient compression of the cuff immediately after the start of measurement, an electrode and a human body may or may not come into contact with each other, or the human body may come into contact with only a small part of the electrode surface or may suddenly come into contact with the entire electrode surface, which is very unstable. This causes a large noise on an electronic circuit that acquires and amplifies the signal of the electrode, and causes a problem that a stable electrocardiographic waveform necessary for the case determination regarding the electrocardiogram cannot be acquired.

In view of the problems as described above, an object of the present invention is to provide a technique that can perform stable measurement of an electrocardiographic waveform in a biometric information measuring device that simultaneously performs blood pressure measurement and measurement of an electrocardiographic waveform. [Citation: Patent Document 1: JP 2014-36843 A]

Solution to Problem

In order to solve the above-mentioned problems, the present invention includes:

a blood pressure measurement unit including a cuff configured to compress a target measurement site of a subject, a pump configured to supply a gas into the cuff, an exhaust valve configured to adjust discharge of the gas from within the cuff, a pressure detection unit configured to detect a cuff pressure that is a pressure in the cuff, a cuff pressure control unit configured to control the pump and the exhaust valve, and a blood pressure calculation unit configured to calculate a blood pressure of the subject, the blood pressure measurement unit being configured to measure the blood pressure of the subject;

an electrocardiographic measurement unit configured to process an electrical signal acquired through a plurality of electrodes contactable to a skin of the subject to measure an electrocardiographic waveform; and an electrocardiographic storage unit configured to store information of the measured electrocardiographic waveform in association with a time, wherein the biometric information measuring device further includes a section designation unit configured to designate a section of the information of the electrocardiographic waveform based on a progress of measurement of the blood pressure of the subject in parallel with measurement of the electrocardiographic waveform from the information of the electrocardiographic waveform stored in the electrocardiographic storage unit.

In the biometric information measuring device that processes electrical signals acquired through a plurality of electrodes including electrodes provided on the target measurement site of the cuff to measure the electrocardiographic waveform in parallel with the measurement of the blood pressure performed by controlling the pressure in the cuff compressing the target measurement site of the subject, the contact state of the electrode provided at the target measurement site of the cuff with the skin of the subject may fluctuate under the influence of a change in the cuff pressure due to the progress of the measurement of the blood pressure. In the present invention, by providing the section designation unit that designates the section of the information of the electrocardiographic waveform based on the progress of the blood pressure measurement in parallel with the measurement of the electrocardiographic waveform with respect to the information of the electrocardiographic waveform stored in the electrocardiographic storage unit in association with a time, it is possible to designate the electrocardiographic waveform measured in a state in which the contact state between the skin of the subject and the electrode are common among the electrocardiographic waveforms acquired over time. In addition, by designating a section in which the contact state between the skin of the subject and the electrode is stable, a section of high-quality electrocardiographic waveform information with little noise can also be designated. By designating the section of the information of the electrocardiographic waveform in this manner, the information of the stable electrocardiographic waveform can be extracted, and thus the stable measurement of the electrocardiographic waveform can be performed. The information of the electrocardiographic waveform extracted in this manner can be used for various purposes such as case determination.

In the present invention, the section designation unit may employ various indices as indices indicating the progress of measurement of the blood pressure of the subject in parallel with measurement of the electrocardiographic waveform. That is, the section of the information of the electrocardiographic waveform may be designated based on the cuff pressure in the measurement of the blood pressure. In addition, the section designation unit may designate the section of the information of the electrocardiographic waveform based on a time progressing in the measurement of the blood pressure. In addition, a pulse wave amplitude calculation unit that calculates a pulse wave amplitude from the cuff pressure detected by the pressure detection unit may further be provided, and the section designation unit may designate the section of the information of the electrocardiographic waveform based on the pulse wave amplitude. In this manner, it is possible to stably measure an electrocardiographic waveform in the biometric information measuring device that measures blood pressure information such as a minimum blood pressure and a maximum blood pressure by calculating the pulse wave amplitude like the oscillometric method. Further, the section designation unit may designate the section of the information of the electrocardiographic waveform based on the blood pressure of the subject calculated by the blood pressure calculation unit. Note that the calculated blood pressure preferably includes at least one of the minimum blood pressure and the maximum blood pressure.

Further, in the present invention, the blood pressure measurement unit may measure the blood pressure of the subject in at least one of a pressurization process of increasing the cuff pressure and a depressurization process of decreasing the cuff pressure.

In this manner, the electrocardiographic waveform can be stably measured both in the biometric information measuring device including the blood pressure measurement unit that measures the blood pressure of the subject in the pressurization process of increasing the cuff pressure, and in the biometric information measuring device including the blood pressure measurement unit that measures the blood pressure of the subject in the depressurization process of decreasing the cuff pressure.

Advantageous Effects of Invention

According to the present invention, it is possible to provide a technique that can perform stable measurement of an electrocardiographic waveform in a measuring device that simultaneously performs blood pressure measurement and measurement of an electrocardiographic waveform.

BRIEF DESCRIPTION OF DRAWINGS

Various embodiments are disclosed, by way of example only, with reference to the accompanying schematic drawings in which corresponding reference symbols indicate corresponding parts, in which:

FIG. 1 is a block diagram illustrating a schematic configuration of a biometric information measuring device according to Example 1.

FIG. 2 is a diagram illustrating a progress of blood pressure measurement and electrocardiographic measurement and a temporal change in a cuff pressure according to Example 1.

FIG. 3 is a diagram illustrating a progress of blood pressure measurement and electrocardiographic measurement and a temporal change in a cuff pressure according to Example 2.

FIG. 4 is a diagram illustrating a progress of blood pressure measurement and electrocardiographic measurement, and a temporal change in a cuff pressure and a pulse wave amplitude according to Example 3.

FIG. 5 is a diagram illustrating a progress of blood pressure measurement and electrocardiographic measurement, and a temporal change in a cuff pressure and a pulse wave amplitude according to Example 4.

FIG. 6 is a diagram illustrating a progress of blood pressure measurement and electrocardiographic measurement and a temporal change in a cuff pressure according to Example 5.

FIG. 7 is a diagram illustrating a progress of blood pressure measurement and electrocardiographic measurement, and a temporal change in a cuff pressure and a pulse wave amplitude according to Example 6.

FIG. 8 is a diagram illustrating a progress of blood pressure measurement and electrocardiographic measurement and a temporal change in a cuff pressure according to Example 7.

FIG. 9 is a diagram illustrating a progress of blood pressure measurement and electrocardiographic measurement and a temporal change in a cuff pressure according to Example 8.

FIG. 10 is a diagram illustrating a progress of blood pressure measurement and electrocardiographic measurement, and a temporal change in a cuff pressure and a pulse wave amplitude according to Example 9.

FIG. 11 is a diagram illustrating a progress of blood pressure measurement and electrocardiographic measurement, and a temporal change in a cuff pressure and a pulse wave amplitude according to Example 10.

FIG. 12 is a diagram illustrating a progress of blood pressure measurement and electrocardiographic measurement and a temporal change in a cuff pressure according to Example 11.

FIG. 13 is a diagram illustrating a progress of blood pressure measurement and electrocardiographic measurement, and a temporal change in a cuff pressure and a pulse wave amplitude according to Example 12.

DESCRIPTION OF EMBODIMENTS

Embodiments of the present invention will be specifically described below with reference to the drawings. It should be noted, however, that the dimension, material, shape, relative arrangement, and the like of the components described in the examples are not intended to limit the scope of this invention to them alone unless otherwise stated.

Example 1. Hereinafter, Example 1 of the present invention will be described.

Configuration of Biometric Information Measuring Device. FIG. 1 is a block diagram illustrating a schematic configuration of a biometric information measuring device 100 according to the present example. The biometric information measuring device 100 mainly includes an electrocardiographic detection unit 110, a blood pressure measurement mechanism unit 120, a control unit 130, an operation unit 140, and a display unit 150.

The electrocardiographic detection unit 110 includes an electrode 111, an electrode 112, and an electrocardiographic measurement circuit 113. The electrode 111 and the electrode 112 are in contact with the skin of a subject and detect an electrical signal. The electrocardiographic measurement circuit 113 includes an amplifier that amplifies the electrical signal detected by the electrode 111 and the electrode 112, an AD conversion circuit that converts an analog signal into a digital signal, and the like. Here, the electrodes to be in contact with the skin of the subject to detect the electrocardiographic waveform are not limited to the two electrodes 111 and 112, and an appropriate number of electrodes can be provided. Here, at least one of the electrode 111 and the electrode 112 is provided on the target measurement site side of a cuff 121 described below. Here, the electrode 111 and the electrode 112 correspond to a plurality of electrodes that can come into contact with the skin of the subject according to the present invention. Further, the electrocardiographic measurement circuit 113 and the electrocardiographic control unit 131 described below constitute an electrocardiographic measurement unit of the present invention.

The blood pressure measurement mechanism unit 120 includes the cuff 121, a pressure sensor 122, a pressure pump 123, a drive circuit 124, and an exhaust valve 125. The cuff 121 is a band-like member and has a bag-like body therein. The pressure sensor 122 is a sensor that measures the cuff pressure, which is a pressure inside the cuff 121, and the output of the pressure sensor 122 is transmitted to a blood pressure measurement control unit 134, which will be described below. The pressure pump 123 pressurizes the cuff 121 by supplying air into the cuff 121. The drive circuit 124 is a circuit that drives the pressure pump 123 based on an instruction from the blood pressure measurement control unit 134. The exhaust valve 125 is a valve that adjusts the amount of air discharged from within the cuff 121 based on an instruction from the blood pressure measurement control unit 134. The cuff 121 is wrapped around the target measurement site such as the wrist or upper arm of the subject. By supplying air from the pressure pump 123 to the cuff 121 with the exhaust valve 125 closed, the cuff 121 is pressurized, and the target measurement site of the subject is compressed. After pressurization to a predetermined pressure, the exhaust valve 125 is opened, the air in the cuff 121 is discharged, and the cuff 121 is depressurized. Here, the cuff 121, the pressure sensor 122, the pressure pump 123, and the exhaust valve 125 respectively correspond to a cuff, a pressure detection unit, a pump, and an exhaust valve of the present invention. Here, air is described as an example of the gas supplied into the cuff 121, but the gas is not limited to this.

The control unit 130 is constituted by, for example, a micro controller unit (MCU) including a CPU and a memory including a main storage unit and an auxiliary storage device. By reading a program stored in the auxiliary storage device into the main storage unit and executing the program in the CPU, each function described below is realized. The control unit 130 may be configured by an application specific integral circuit (ASIC), a field programmable gate array (FPGA), or the like.

The control unit 130 includes an electrocardiographic control unit 131, a storage unit 132, a case determination section determination unit 133, the blood pressure measurement control unit 134, a pulse wave amplitude calculation unit 135, a blood pressure calculation unit 136, and a display control unit 137.

The electrocardiographic control unit 131 performs predetermined arithmetic processing on the data acquired through the electrode 111 and the electrode 112 and processed by the electrocardiographic measurement circuit 113 to measure an electrocardiographic waveform. Information of the electrocardiographic waveform measured by the electrocardiographic control unit 131 is stored in the storage unit 132 in association with a time. The case determination section determination unit 133 determines a case determination section for extracting a portion to be used for case determination in the information of the electrocardiographic waveform stored in the storage unit 132 based on information from the pulse wave amplitude calculation unit 135 or the blood pressure calculation unit 136 to be described below. Here, the storage unit 132 corresponds to an electrocardiographic storage unit of the present invention. The case determination section determination unit corresponds to a section designation unit of the present invention.

The blood pressure measurement control unit 134 acquires information of the cuff pressure measured by the pressure sensor 122, and controls the drive circuit 124 and the exhaust valve 125. Based on the information of the cuff pressure acquired by the blood pressure measurement control unit 134, the pulse wave amplitude calculation unit 135 calculates the pulse wave amplitude, and the blood pressure calculation unit 136 calculates the blood pressure including the maximum blood pressure (systolic blood pressure) and the minimum blood pressure (diastolic blood pressure). Here, the blood pressure is measured by an oscillometric method. That is, at the time of pressurization control for increasing the cuff pressure or at the time of depressurization control for decreasing the cuff pressure, the pulse wave amplitude calculation unit 135 calculates the pulse wave amplitude obtained from the cuff pressure, and the blood pressure calculation unit 136 calculates the maximum blood pressure and the minimum blood pressure based on the change in the pulse wave amplitude calculated in this manner. The information regarding the blood pressure calculated by the blood pressure calculation unit 136 is transmitted to the display control unit 137 that controls the display unit 150. In the display control unit 137, image information including information regarding the blood pressure is generated and displayed on the display unit 150. Here, the blood pressure measurement control unit 134, the pulse wave amplitude calculation unit 135, and the blood pressure calculation unit 136 correspond to a cuff pressure control unit, a pulse wave amplitude calculation unit, and a blood pressure calculation unit of the present invention, respectively. The blood pressure measurement unit of the present invention includes the cuff 121, the pressure sensor 122, the pressure pump 123, the exhaust valve 125, the blood pressure measurement control unit 134, the pulse wave amplitude calculation unit 135, and the blood pressure calculation unit 136.

The operation unit 140 includes an operation instruction unit such as a button or a switch, and receives an instruction to start blood pressure and electrocardiographic measurement, various setting inputs, and the like. The display unit 150 includes, for example, an image display unit such as a liquid crystal display, and displays measurement information such as the maximum blood pressure, the minimum blood pressure, the pulse, and the electrocardiographic waveform, and various kinds of information such as an operation guidance and a notification of abnormality. Information necessary for determining the case determination section may be displayed on the display unit 150 so that the subject can select and set the case determination section through the operation unit 140, or the operator may set a default value at the time of shipment.

FIG. 2 is a diagram illustrating the progress of blood pressure measurement and electrocardiographic measurement and the temporal change of the cuff pressure when the electrocardiographic measurement is performed simultaneously with the blood pressure measurement. Here, the blood pressure is measured in the process of increasing the cuff pressure (pressurization process). From a measurement start time point T0, the exhaust valve 125 is closed and the pressure pump 123 is driven to gradually increase the cuff pressure. At a time point Tp when the cuff pressure is increased to the predetermined pressure, the driving of the pressure pump 123 is stopped, and the blood pressure measurement is finished. Next, the exhaust valve 125 is opened, the air in the cuff 121 is rapidly discharged, and the cuff pressure also rapidly decreases.

Here, the blood pressure and the electrocardiographic waveform are simultaneously measured. Therefore, the measurement of the blood pressure proceeds in parallel with the measurement of the electrocardiographic waveform. While the electrocardiographic waveform is continuously measured in the process of pressurizing the cuff 121 from the measurement start time point T0, the case determination section determination unit 133 determines a case determination section based on various indices indicating the progress of blood pressure measurement in the information of the electrocardiographic waveform measured over time in this manner, thereby designating a certain section (temporal range). By designating a certain section of the information of the electrocardiographic waveform based on the indices indicating the progress of the measurement of the blood pressure, it is possible to extract the electrocardiographic waveform when the skin of the subject is in a certain contact state with the electrode 111 and the electrode 112. Therefore, the electrocardiographic waveform can be stably measured. Examples of such a certain section include a section in which a stable electrocardiographic waveform suitable for case determination can be measured, but an appropriate section can also be designated in accordance with the purpose of processing and use of the electrocardiographic waveform.

In the case determination section determining method according to Example 1, as illustrated in FIG. 2, a time point Ds1 at which the cuff pressure is equal to or greater than a predetermined pressure Ps1 is set as the start point of the case determination section. For the case determination section, only the start point may be determined. At this time, for example, the end time point Tp of the pressurization process can be set as the end point of the case determination section. Alternatively, the end point of the case determination section may be set to a time point De1 at which the cuff pressure is equal to or greater than a predetermined pressure Pe1 that is equal to or greater than the pressure Ps1.

Example 2. Example 2 will be described below. Since this Example is the same as Example 1 except for the method of determining the case determination section, a description of the configuration of the biometric information measuring device will be omitted.

FIG. 3 is a diagram illustrating the progress of blood pressure measurement and electrocardiographic measurement and the temporal change of the cuff pressure when the electrocardiographic measurement is performed simultaneously with the blood pressure measurement. Here, a time point Ds2 at which a predetermined time T21 has elapsed from the start time point T0 of the blood pressure measurement and the electrocardiographic measurement is set as the start point of the case determination section. For the case determination section, only the start point may be determined. At this time, for example, the end time point Tp of the pressurization process may be set as the end point. In addition, a time point De2 at which a predetermined time T22 has elapsed from the time point Ds2 at which the time T21 has elapsed from the start of measurement may be set as the end point of the case determination section.

By determining the case determination section in this manner, stable electrocardiographic measurement can be performed.

Example 3. Example 3 will be described below. Since this Example is the same as Example 1 except for the method of determining the case determination section, a description of the configuration of the biometric information measuring device will be omitted.

FIG. 4 is a diagram illustrating the progress of blood pressure measurement and electrocardiographic measurement and the temporal change of the cuff pressure and the pulse wave amplitude when the electrocardiographic measurement is performed simultaneously with the blood pressure measurement. Here, a time point Ds3 at which the pulse wave amplitude is equal to or greater than a predetermined value As3 is set as the start point of the case determination section. For the case determination section, only the start point may be determined. At this time, for example, the end time point Tp of the pressurization process may be set as the end point. Alternatively, the end point of the case determination section may be set to a time point De3 at which the cuff pressure is higher than a pressure Ps3 at which the pulse wave amplitude is equal to or greater than the predetermined value As3, and at which the pulse wave amplitude is equal to or smaller than a predetermined value Ae3. By determining the case determination section in this manner, stable electrocardiographic measurement can be performed.

Example 4. Example 4 will be described below. Since this Example is the same as Example 1 except for the method of determining the case determination section, a description of the configuration of the biometric information measuring device will be omitted.

FIG. 5 is a diagram illustrating the progress of blood pressure measurement and electrocardiographic measurement and the temporal change of the cuff pressure and the pulse wave amplitude when the electrocardiographic measurement is performed simultaneously with the blood pressure measurement. Here, a time point Ds4 at which the pulse wave amplitude is equal to or greater than a predetermined value As4 and the pulse wave amplitudes equal to or greater than the predetermined value As4 continue is set as the start point of the case determination section. For the case determination section, only the start point may be determined. At this time, for example, the end time point Tp of the pressurization process may be set as the end point. Alternatively, the end point of the case determination section may be set to a time point De4 at which the cuff pressure is higher than a pressure Ps4 at the time point Ds4 at which the pulse wave amplitude is equal to or greater than the predetermined value As4 and the pulse wave amplitudes equal to or greater than the predetermined value As4 continue, and at which the pulse wave amplitude is equal to or smaller than a predetermined value Ae4 and the pulse wave amplitudes equal to or smaller than the predetermined value Ae4 continue.

By determining the case determination section in this manner, stable electrocardiographic measurement can be performed.

Example 5. Example 5 will be described below. Since this Example is the same as Example 1 except for the method of determining the case determination section, a description of the configuration of the biometric information measuring device will be omitted.

FIG. 6 is a diagram illustrating the progress of blood pressure measurement and electrocardiographic measurement and the temporal change of the cuff pressure when the electrocardiographic measurement is performed simultaneously with the blood pressure measurement. Here, a section including time points at which a minimum blood pressure Dp5 and a maximum blood pressure Sp5 are detected in the blood pressure measurement, that is, a section having a time point Ds5 before a time point TD5 at which the minimum blood pressure Dp5 is detected as a start point and a time point De5 after a time point TS5 at which the maximum blood pressure Sp5 is detected as an end point, is determined as the case determination section. By determining the case determination section in this manner, stable electrocardiographic measurement can be performed.

Example 6. Example 6 will be described below. Since this Example is the same as Example 1 except for the method of determining the case determination section, a description of the configuration of the biometric information measuring device will be omitted.

FIG. 7 is a diagram illustrating the progress of blood pressure measurement and electrocardiographic measurement and the temporal change of the cuff pressure and the pulse wave amplitude when the electrocardiographic measurement is performed simultaneously with the blood pressure measurement. Here, a predetermined time or pressure before and after a specific feature of the pulse wave amplitude as a starting point is determined as the case determination section. As the specific feature of the pulse wave amplitude, various features can be selected, but in the example illustrated in FIG. 7, the maximum amplitude is used as the feature. A time point T6 at which the pulse wave amplitude is at a maximum is set as a starting point, a time point Ds6 preceding the starting point by a time Tb6 is set as a start point of the case determination section, and a time point De6 after the elapse of a time Ta6 from the time point T6 is set as an end point of the case determination section. The starting point may be set to the time point T6 at which the pulse wave amplitude is at a maximum, the start point of the case determination section may be set to a time point at which the cuff pressure is lower than the cuff pressure at the time point T6 by a predetermined value, and the end point of the case determination section may be set to a time point at which the cuff pressure is higher than the cuff pressure at the time point T6 by a predetermined value. By determining the case determination section in this manner, stable electrocardiographic measurement can be performed.

Example 7. Example 7 will be described below. Since this Example is the same as Example 1 except for the method of determining the case determination section, a description of the configuration of the biometric information measuring device will be omitted. In Example 1 to Example 6, the method of determining the case determination section has been described for the case where the blood pressure is measured in the process of increasing the cuff pressure. In the oscillometric method, the exhaust valve 125 is closed, the pressure pump 123 is driven to supply air to the cuff 121 to pressurize the cuff 121 to a predetermined pressure, and the opening degree of the exhaust valve 125 is adjusted to gradually discharge the air. Thus, the blood pressure can be measured in the process of reducing the cuff pressure (depressurization process). In the following example, a method of determining a case determination section will be described for the case where the blood pressure is measured in the process of reducing the cuff pressure.

FIG. 8 is a diagram illustrating the progress of blood pressure measurement and electrocardiographic measurement and the temporal change of the cuff pressure when the electrocardiographic measurement is performed simultaneously with the blood pressure measurement. Here, as described above, the blood pressure is measured in the process of reducing the cuff pressure. From the measurement start time point T0, the exhaust valve 125 is closed and the pressure pump 123 is driven to rapidly increase the cuff pressure. At a time point Tp0 when the cuff pressure is increased to the predetermined pressure, the driving of the pressure pump 123 is stopped. Then, in a state where the pressure pump 123 is stopped, the opening degree of the exhaust valve 125 is controlled, the air in the cuff 121 is gradually discharged, and the cuff pressure is gradually decreased.

The electrocardiographic waveform is continuously measured from the measurement start time point T0, and the case determination section determination unit 133 determines a case determination section which is a section in which a stable electrocardiographic waveform suitable for the case determination can be measured.

A case determination section determination method according to Example 7 will be described. As illustrated in FIG. 8, a time point Ds7 at which the gradually decreased cuff pressure is equal to or smaller than a predetermined pressure Ps7 is set as a start point of the case determination section. For the case determination section, only the start point may be determined. At this time, for example, the end time point Tp of the blood pressure measurement can be set as the end point of the case determination section. Alternatively, the end point of the case determination section may be set to a time point De7 at which the cuff pressure is equal to or smaller than a predetermined pressure Pe7 that is equal to or smaller than the pressure Ps7. By determining the case determination section in this manner, stable electrocardiographic measurement can be performed.

Example 8. Example 8 will be described below. Since this Example is the same as Example 1 except for the method of determining the case determination section, a description of the configuration of the biometric information measuring device will be omitted.

FIG. 9 is a diagram illustrating the progress of blood pressure measurement and electrocardiographic measurement and the temporal change of the cuff pressure when the electrocardiographic measurement is performed simultaneously with the blood pressure measurement. Here, a time point Ds8 at which a predetermined time T81 has elapsed from the start time point T0 of the blood pressure measurement and the electrocardiographic measurement is set as the start point of the case determination section. For the case determination section, only the start point may be determined. At this time, for example, the end time point Tp of the blood pressure measurement can be set as the end point of the case determination section. Alternatively, a time point Deb at which a predetermined time T82 has elapsed from the time point Ds8 at which the time T81 has elapsed from the start of measurement may be set as the end point of the case determination section. By determining the case determination section in this manner, stable electrocardiographic measurement can be performed.

Example 9. Example 9 will be described below. Since this Example is the same as Example 1 except for the method of determining the case determination section, a description of the configuration of the biometric information measuring device will be omitted.

FIG. 10 is a diagram illustrating the progress of blood pressure measurement and electrocardiographic measurement and the temporal change of the cuff pressure and the pulse wave amplitude when the electrocardiographic measurement is performed simultaneously with the blood pressure measurement. Here, a time point Ds9 at which the pulse wave amplitude is equal to or greater than a predetermined value As9 is set as the start point of the case determination section. For the case determination section, only the start point may be determined. At this time, for example, the end time point Tp of the blood pressure measurement can be set as the end point of the case determination section. Alternatively, the end point of the case determination section may be set to a time point De9 at which the cuff pressure is lower than a pressure Ps9 at which the pulse wave amplitude is equal to or greater than the predetermined value As9, and at which the pulse wave amplitude is equal to or smaller than a predetermined value Ae9. By determining the case determination section in this manner, stable electrocardiographic measurement can be performed.

Example 10. Example 10 will be described below. Since this Example is the same as Example 1 except for the method of determining the case determination section, a description of the configuration of the biometric information measuring device will be omitted.

FIG. 11 is a diagram illustrating the progress of blood pressure measurement and electrocardiographic measurement and the temporal change of the cuff pressure and the pulse wave amplitude when the electrocardiographic measurement is performed simultaneously with the blood pressure measurement. Here, a time point Ds10 at which the pulse wave amplitude is equal to or greater than a predetermined value As10 and the pulse wave amplitudes equal to or greater than the predetermined value As10 continue is set as the start point of the case determination section. For the case determination section, only the start point may be determined. At this time, for example, the end time point Tp of the blood pressure measurement can be set as the end point of the case determination section. Alternatively, the end point of the case determination section may be set to a time point De10 at which the cuff pressure is lower than a pressure Ps10 at the time point Ds10 at which the pulse wave amplitude is equal to or greater than the predetermined value As10 and the pulse wave amplitudes equal to or greater than the predetermined value As10 continue, and at which the pulse wave amplitude is equal to or smaller than a predetermined pulse wave amplitude Ae10 and the pulse wave amplitudes equal to or smaller than the predetermined value Ae10 continue. By determining the case determination section in this manner, stable electrocardiographic measurement can be performed.

Example 11. Example 11 will be described below. Since this Example is the same as Example 1 except for the method of determining the case determination section, a description of the configuration of the biometric information measuring device will be omitted.

FIG. 12 is a diagram illustrating the progress of blood pressure measurement and electrocardiographic measurement and the temporal change of the cuff pressure when the electrocardiographic measurement is performed simultaneously with the blood pressure measurement. Here, a section including time points at which a maximum blood pressure Sp11 and a minimum blood pressure Dp11 are detected in the blood pressure measurement, that is, a section having a time point Ds11 before a time point TS11 at which the maximum blood pressure Sp11 is detected as a start point and a time point De11 after a time point TD11 at which the minimum blood pressure Dp11 is detected as an end point, is determined as the case determination section. By determining the case determination section in this manner, stable electrocardiographic measurement can be performed.

Example 12. Example 12 will be described below. Since this Example is the same as Example 1 except for the method of determining the case determination section, a description of the configuration of the biometric information measuring device will be omitted.

FIG. 13 is a diagram illustrating the progress of blood pressure measurement and electrocardiographic measurement and the temporal change of the cuff pressure and the pulse wave amplitude when the electrocardiographic measurement is performed simultaneously with the blood pressure measurement. Here, a predetermined time or pressure before and after a specific feature of the pulse wave amplitude as a starting point is determined as the case determination section. As the specific feature of the pulse wave amplitude, various features can be selected, but in the example illustrated in FIG. 13, the maximum amplitude is used as the feature. A time point T12 at which the pulse wave amplitude is at a maximum is set as a starting point, a time point Ds12 preceding the starting point by a time Tb12 is set as a start point of the case determination section, and a time point De12 after the elapse of a time Ta12 from the time point T12 is set as an end point of the case determination section. The starting point may be set to the time point T12 at which the pulse wave amplitude is at a maximum, the start point of the case determination section may be set to a time point at which the cuff pressure is lower than the cuff pressure at the time point T12 by a predetermined value, and the end point of the case determination section may be set to a time point at which the cuff pressure is higher than the cuff pressure at the time point T12 by a predetermined value. By determining the case determination section in this manner, stable electrocardiographic measurement can be performed.

REFERENCE NUMERALS LIST

100 Biometric information measuring device
111, 112 Electrode
113 Electrocardiographic measurement circuit
121 Cuff
122 Pressure sensor
123 Pressure pump
124 Drive circuit
125 Exhaust valve
131 Electrocardiographic control unit
132 Storage unit
133 Case determination section determination unit
134 Blood pressure measurement control unit
135 Pulse wave amplitude calculation unit
136 Blood pressure calculation unit

What is claimed is:

1. A biometric information measuring device that simultaneously measures a blood pressure and an electrocardiographic waveform of a subject comprising:

a blood pressure measurement unit including a cuff configured to compress a target measurement site of the subject, a pump configured to supply a gas into the cuff, an exhaust valve configured to adjust discharge of the gas from within the cuff, a pressure detection unit configured to detect a cuff pressure that is a pressure in the cuff, a cuff pressure control unit configured to control the pump and the exhaust valve, and the blood pressure calculation unit configured to calculate a blood pressure of the subject, the blood pressure measurement unit being configured to measure the blood pressure of the subject in at least one of a pressurization process of increasing the cuff pressure and a depressurization process of decreasing the cuff pressure;

an electrocardiographic measurement unit configured to process an electrical signal acquired through a plurality of electrodes contactable to a skin of the subject to measure the electrocardiographic waveform; and an electrocardiographic storage unit configured to store information of the measured electrocardiographic waveform in association with a time, wherein the biometric information measuring device further includes a section designation unit configured to designate a section of high-quality information of the electrocardiographic waveform with little noise in at least one of the pressurization process and the depressurization process based on a progress of measurement of the blood pressure of the subject in parallel with measurement of the electrocardiographic waveform from the information of the electrocardiographic waveform stored in the electrocardiographic storage unit.

2. The biometric information measuring device according to claim 1, wherein the section designation unit is configured to designate the section of the high-quality information of the electrocardiographic waveform based on the cuff pressure in the measurement of the blood pressure.

3. The biometric information measuring device according to claim 1, wherein the section designation unit is configured to designate the section of the high-quality information of the electrocardiographic waveform based on a time progressing in the measurement of the blood pressure.

4. The biometric information measuring device according to claim 1, further comprising a pulse wave amplitude calculation unit configured to calculate a pulse wave amplitude from the cuff pressure detected by the pressure detection unit, wherein the section designation unit is configured to designate the section of the high-quality information of the electrocardiographic waveform based on the pulse wave amplitude.

5. The biometric information measuring device according to claim 1, wherein the section designation unit is configured to designate the section of the high-quality information of the electrocardiographic waveform based on the blood pressure of the subject calculated by the blood pressure calculation unit.

* * * * *